Figure 1:
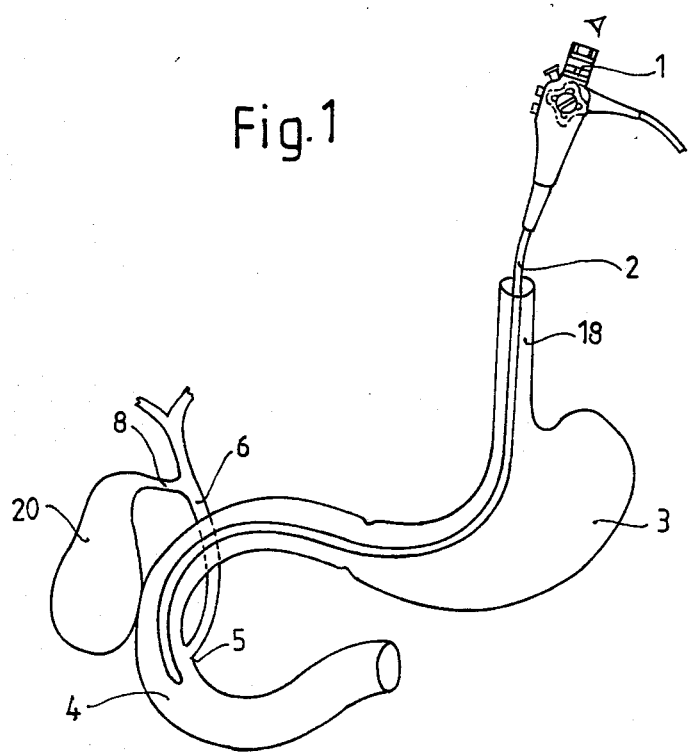

United States Patent [19]

Foerster et al.

[11] Patent Number: 4,905,667

[45] Date of Patent: Mar. 6, 1990

[54] APPARATUS FOR ENDOSCOPIC-TRANSPAPILLARY EXPLORATION OF BILIARY TRACT

[76] Inventors: Ernst Foerster, Lachnerstrasse 71; Wolfram Domschke, Ebrardstrasse 1, both of Erlangen, Fed. Rep. of Germany, 8520

[21] Appl. No.: 301,754

[22] PCT Filed: May 10, 1988

[86] PCT No.: PCT/DE88/00279

§ 371 Date: Dec. 1, 1988

§ 102(e) Date: Dec. 1, 1988

[87] PCT Pub. No.: WO88/08726

PCT Pub. Date: Nov. 17, 1988

[30] Foreign Application Priority Data

May 12, 1987 [DE] Fed. Rep. of Germany ....... 3715699

[51] Int. Cl.$^4$ ................................................ A61B 1/00
[52] U.S. Cl. ......................................... 128/4; 604/280
[58] Field of Search .................. 128/3, 4, 5, 6, 7, 8; 604/280

[56] References Cited

U.S. PATENT DOCUMENTS

| | | | |
|---|---|---|---|
| 3,057,345 | 10/1962 | Ferris et al. | 128/8 |
| 3,973,556 | 8/1976 | Fleischacker et al. | 128/772 |
| 4,033,331 | 7/1977 | Guss et al. | 128/657 |
| 4,253,467 | 3/1981 | Frazier | 128/4 |
| 4,774,949 | 10/1988 | Fogarty | 128/4 X |
| 4,800,870 | 1/1989 | Reid, Jr. | 128/6 |

FOREIGN PATENT DOCUMENTS

| | | |
|---|---|---|
| 132215 | 6/1984 | European Pat. Off. . |
| 3004335 | 8/1980 | Fed. Rep. of Germany . |
| 2923633 | 12/1980 | Fed. Rep. of Germany . |
| 3447642 | 9/1986 | Fed. Rep. of Germany . |

OTHER PUBLICATIONS

Percutaneous Transfemoral Selective Coronary Arteriography, by Melvin Judkins, M.D. Radiology clinics of North America. vol. VI, No. 3, Dec. 1968, p. 467.

Primary Examiner—William H. Grieb
Attorney, Agent, or Firm—Fleit, Jacobson, Cohn, Price, Holman & Stern

[57] ABSTRACT

An apparatus where a side-view duodenoscope 2 is provided, a probe catheter is slidable through the side-view duodenoscope 2 and a guide wire is provided for arrangement in the side-view duodenoscope 2 and the probe catheter. The objective is to ensure reliable, systematic and reproducible representation of the gall bladder lumen by endoscopic-retrograde means. This is achieved in that a guide catheter is slidable over the guide wire while a probe wire 12 is slidable through the guide catheter into the gall bladder luman 20. The probe wire 12 permits a small endoscope or an irrigation catheter to be passed into the gall bladder lumen.

6 Claims, 6 Drawing Sheets

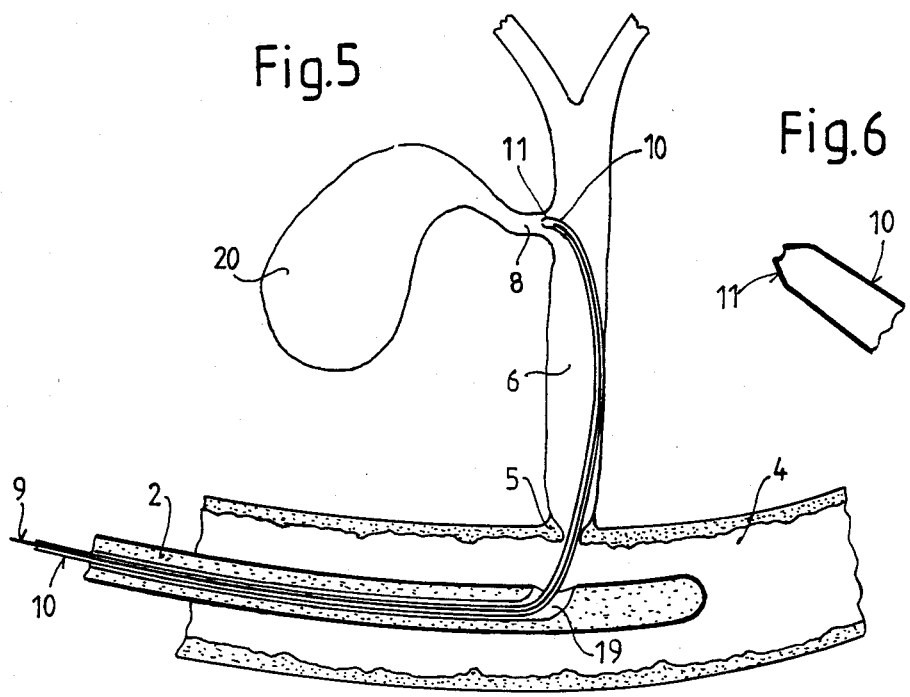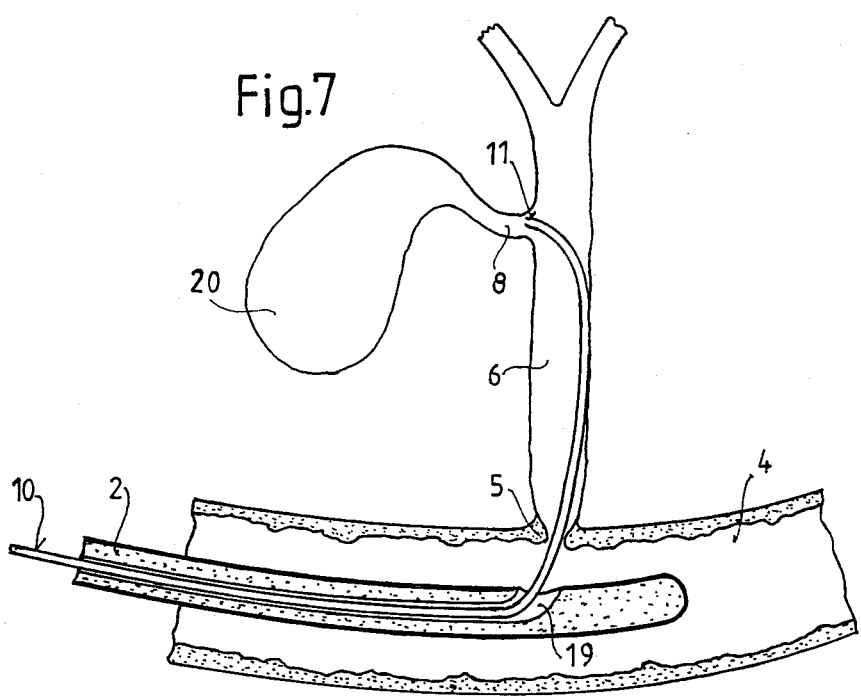

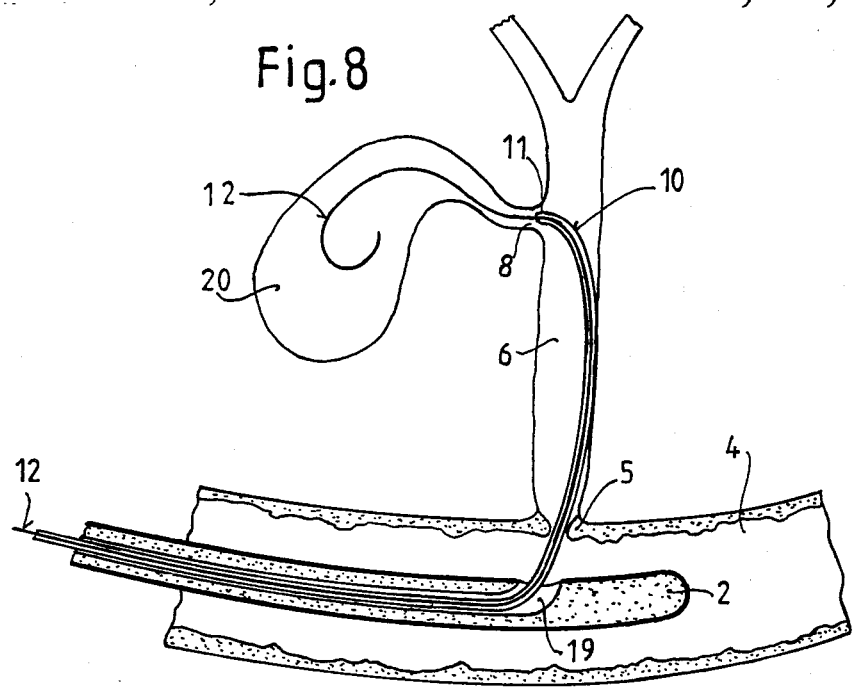
Fig. 8
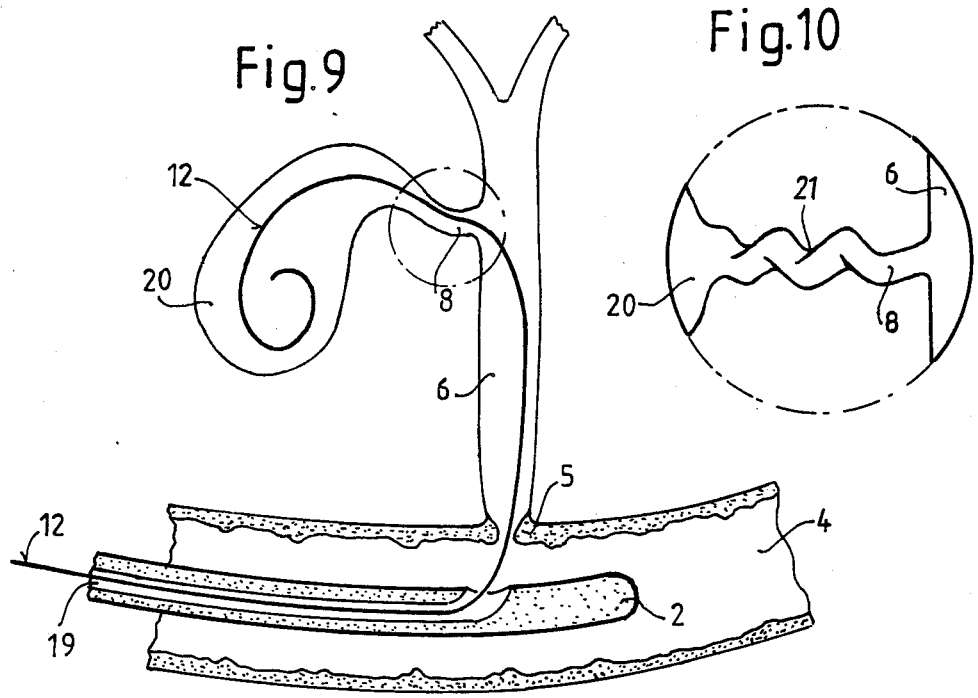
Fig. 9
Fig. 10

APPARATUS FOR ENDOSCOPIC-TRANSPAPILLARY EXPLORATION OF BILIARY TRACT

CROSS REFERENCE TO RELATED APPLICATION(S)

This U.S. application stems from PCT International Application No. PCT/DE88/00279 filed May 10, 1988.

The invention relates to an apparatus for the endoscopic-transpapillary exploration of a biliary tract where a side-view duodenoscope is provided for introduction into the duodenum with its distal end at the duodenal papilla, where a probe catheter is slidable through the side-view duodenoscope and the duodenal papilla into the common bile duct and where a guide wire is provided for arrangement in the side-view duodenoscope and the probe catheter.

A known apparatus (DE-PS 34 47 642) of this type only comprises the side-view duodenoscope, the probe catheter and the guide wire and permits only an examination of the common bile duct. There is, however, the problem of reliable and reproducible representation of the human gall bladder by endoscopic-transpapillary means. A known method is the percutaneous transhepatic puncture and drainage of the gall bladder. This method has its drawbacks in that an artificial access has to be provided through the skin, the risk of tissue injuries is quite high and the stress condition for the patient is correspondingly problematic.

It is the object of the present invention to provide an apparatus of the type initially referred to which permits reliable, systematic and reproducible representation of the gall bladder lumen by endoscopic-retrograde means. In overcoming this problem, the apparatus according to the invention is characterized in that the probe catheter and the guide wire are suitably constructed to be advanced as far as the cystic duct, in that a guide catheter is provide to slide over the guide wire, in that the probe catheter is preformed with bends corresponding to the Judkins or right-coronary catheter and is formed with a conically shaped tip which, with the guide wire retracted, is deflected into the cystic duct, in that a probe wire with a flexible tip piece is slidable through the guide catheter and through the cystic duct into the gall bladder lumen and in that, with the guide catheter retracted, an irrigating catheter or a small endoscope is capable of being slid by means of the probe wire into the gall bladder lumen.

The apparatus according to the invention permits reliable exploration of the cystic duct, the outlet passage of the gall bladder, although the cystic duct which has a diameter of abt. 1-2 mm is difficult to find and, moreover, has a spiral configuration and is narrowed by several valves, the so-called Heister valves, which open in the direction of the gall bladder lumen. The apparatus warrants reliable, systematic manipulation for the exploration of the cystic duct. The parts of the apparatus are introduced by a commercial side-view dudenoscope.

The proportioning of the preforming of the guide catheter corresponds to the branches of the biliary tract. The probe wire is constructed with a distal end that is easily bent while the remainder is stiff and not easily bent. The flexibility serves to bypass obstructions. The balloon of the irrigation catheter serves for the closure of the gall bladder and irrigation for the endoscopic transpapillary lysis of gall stones.

It is specially desirable and advantageous if the irrigation catheter is formed with several conduits for irrigation, evacuation and dilation. This facilitates the operation of the irrigation catheter.

It is also specially desirable and advantageous if the small endoscope is provided with a guide rail or a working conduit for sliding it up onto the probe wire. This facilitates its operation. Alternatively, it is possible to slide an auxiliary catheter over the probe wire and, on retraction of the probe wire, to slide the small endoscope through the auxiliary catheter.

Furthermore, it is specially desirable and advantageous if the flexible tip piece is formed by a spiral wire and provided on its outside with a smooth plastic coating. The plastic coating prevents tissue being squeezed between the wire coils as the spiral wire piece flexes.

Moreover, it is specially desirable and advantageous if the distal end of the probe wire is provided with a smooth round tip piece. This so-called Kaltenbach tip is a simple means of constructing the probe wire with a smooth rounded distal end.

The apparatus according to the invention is used to perform a procedure for the endoscopic transpapillary exploration of the gall bladder, whereby a side-view duodenoscope is introduced into the duodendum with its distal end at the duodenal papilla, whereby a probe catheter is slid through the side-view duodenoscope and the duodenal papilla into the common gall duct as far as the opending of the cystic duct, whereby a guide wire is advanced through the probe catheter, and then the probe catheter is retracted, whereby a guide catheter is slid over the guide wire, this guide catheter being preformed similar to the Judkins or right coronary catheter with proportions matching the branches of the gall bladder and constructed with a conically shaped tip, whereby, upon retraction of the guide wire, the conical tip of the guide catheter is deflected into the cystic duct due to the guide catheter being preformed, whereby a probe wire is slidable through the guide catheter and the cystic duct into the gall bladder and whereby a tool is inserted into the gall bladder by means of the probe wire and then the probe wire is withdrawn.

Figure 2:
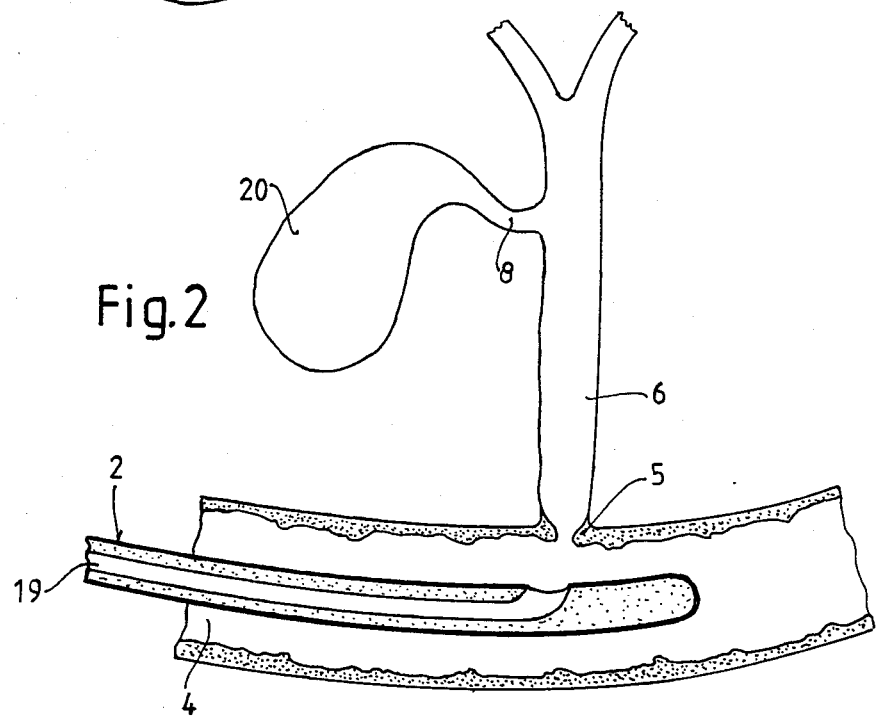
Figure 3:
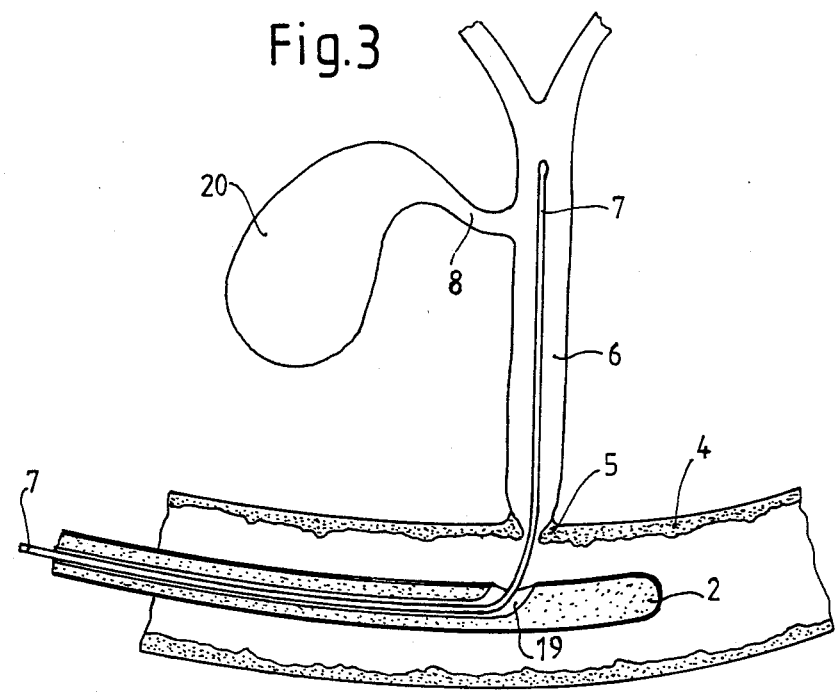
Figure 4:
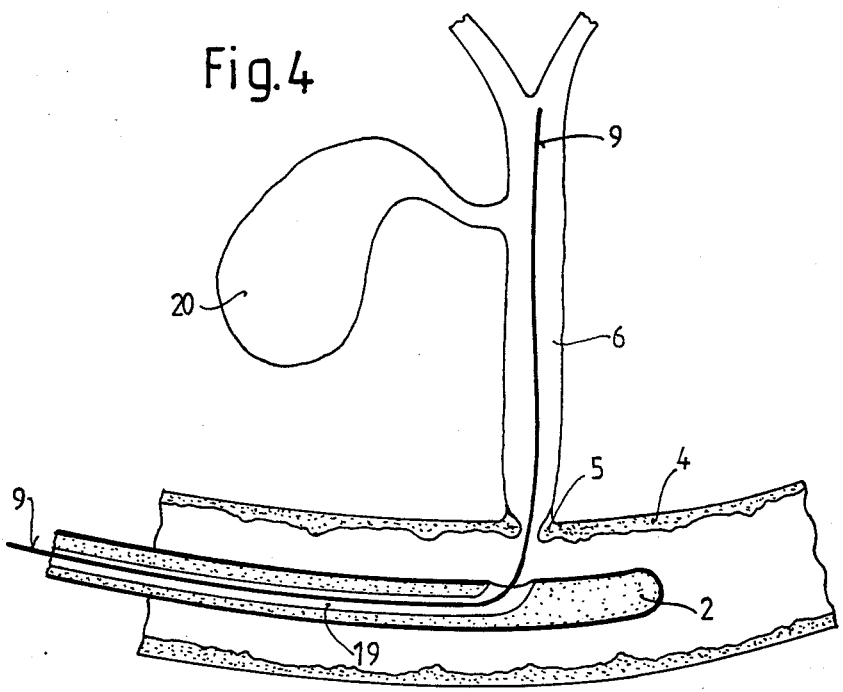
Figure 11:
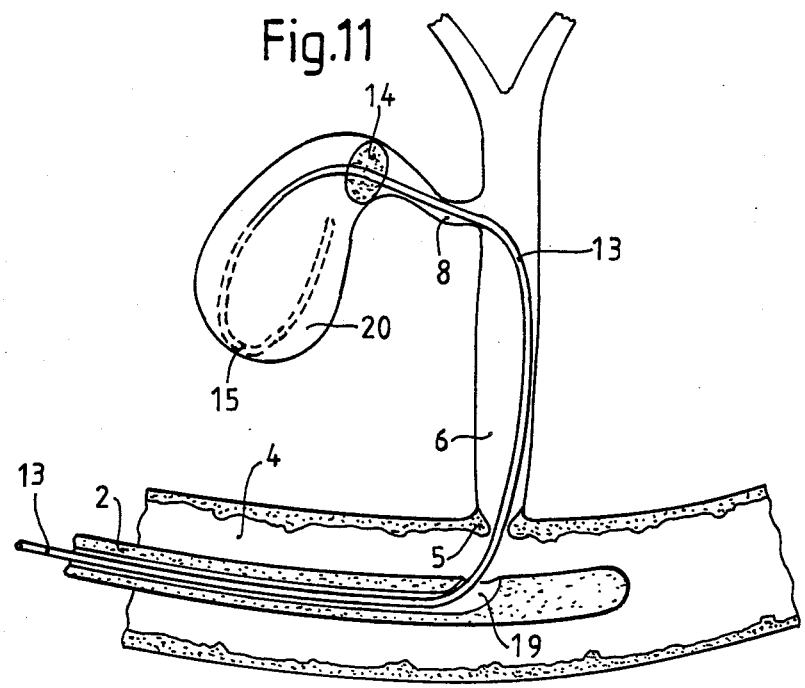
Figure 12:
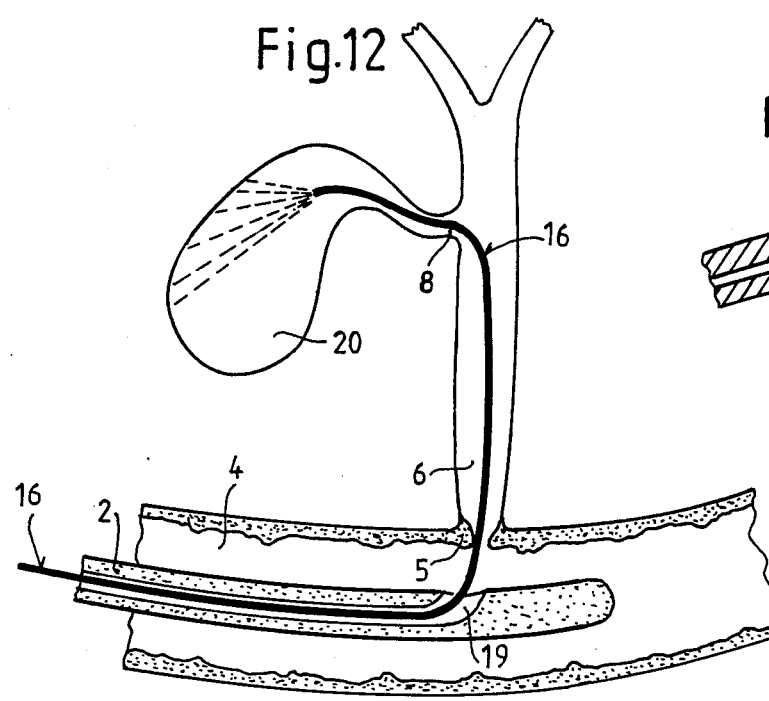
Figure 13:
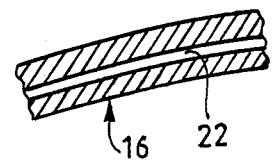
Figure 14:
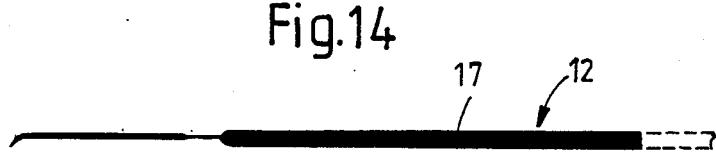

A preferred embodiment of the invention is shown in the accompanying drawing, that is, an apparatus for the endoscopic transpapillary exploration of a biliary tract. In the drawing:

FIG. 1 is a side-view duodenoscope of the apparatus in the biliary tract,

FIG. 2 shows the side-view duodenoscope according to FIG. 1 drawn on a larger scale than FIG. 1, FIG. 3 a probe catheter in the biliary tract, FIG. 4 a guide wire in the biliary tract FIG. 5 a guide catheter in the biliary tract with the guide wire partially retracted, FIG. 6 the tip of the guide catheter drawn on a larger scale than FIG. 5, FIG. 7 the guide catheter according to FIG. 5 with the guide wire completely retracted, FIG. 8 a probe wire in the biliary tract, threaded through the guide catheter, FIG. 9 the probe wire according to FIG. 8 with the guide catheter retracted, FIG. 10 a detail of FIG. 9 drawn on a larger scale than FIG. 9, FIG. 11 an irrigation catheter in the biliary tract with the guide wire retracted, FIG. 12 a small endoscope in the biliary tract with the guide wire retracted, FIG. 13 a section through part of the small endoscope drawn a larger scale than FIG. 12, FIG. 14 the distal end piece of the probe wire drawn on a larger scale than FIG. 8

Figure 15:
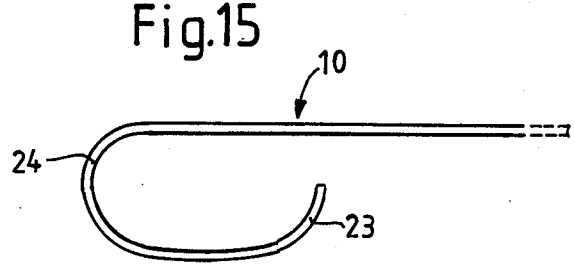
Figure 16:
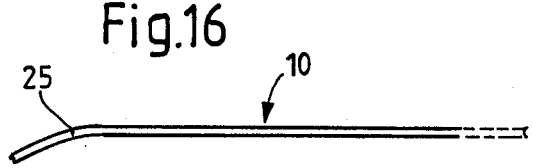

FIG. 15 a Judkins catheter,

FIG. 16 a catheter with a bent end and

Figure 17:
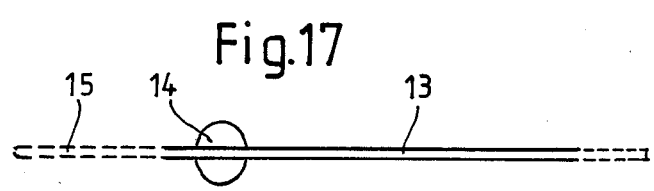

FIG. 17 the irrigation catheter drawn on a larger scale than FIG. 11.

According to FIGS. 1 and 2 ther is provided a side-view duodenoscope 2 provided with an eyepiece 1, the duodenoscope being inserted through an esophagus 18 and a stomach 3 into a duodendum 4 as far as the duodenal papilla 5. FIGS. 1 and 2 thus show the anatomical conditions with a side-view duodenoscope 2 introduced which is formed with a working conduit 19. Branching off at the duodenal papilla 5 is the common bile duct 6 into which a probe catheter 7 is introduced via the working conduit 19 according to FIG. 3. Via the working or instrumentation conduit 19 of the side-view duodenoscope 2 introduced through the gastro-duodenal passage as far as the duodenal papilla 5, the probe catheter 7 is passed into the common bile duct 6 permitting contrast media visualization and X-ray examination of the intra- and extra-hepatitic biliary ducts. The probe catheter 7 is similar in construction to a TEFLON catheter as generally used for the exploration of the common bile duct.

Branching off the common bile duct 6 is the cystic duct 8 which unites with the gall bladder lumen 20. The probe catheter 7 has been passed with its distal end slightly past the cystic duct 8. A guide wire 9 is inserted through the probe catheter 7 which is then retracted or withdrawn whereupon the guide wire 9 resides in the common bile duct 6 as shown in FIG. 4. The guide wire 9 is similar in construction to a metal spiral wire as commonly used for the exploration of the common bile duct. As shown in FIG. 5, a guide catheter 10 is now passed through the working conduit 19 over the guide wire 9 into the common bile duct 6. According to FIG. 5, the guide wire 9 has been partially retracted. The guide catheter 10 is formed with a conical tip 11 as illustrated in FIG. 6. FIG. 7 shows the guide wire 9 completely retracted and the guide catheter 10 occluding with its conical tip 11 the opening of the cystic duct 8 into the common bile duct 6.

According to FIG. 8, a probe wire 12 is advanced through the guide catheter 10 inserted in the common bile duct 6 to enter the cystic duct 8 and the gall bladder lumen 20. The guide catheter 10 is then retracted and withdrawn while the probe wire is left in the gall bladder lumen 20 as indicated in FIG. 9. FIG. 10 shows the detailed anatomical conditions at the cystic duct 8 which usually has a spiral configuration and is lined with the Heister valves 21.

FIG. 11 shows an irrigation catheter 13 advanced into the gall bladder lumen 20. The irrigation catheter 13 is passed into the gall bladder lumen 20 via the probe wire 12 which is subsequently withdrawn. Alternatively, a small endoscope 16 is passed over the probe wire 12 into the gall bladder lumen 20 and, subsequently, the probe wire 20 is withdrawn. The small endoscope 16 is formed with a commonly used optical device and, according to FIG. 13, with a guiding working conduit 22 which accommodates the probe wire 12.

FIG. 14 illustrates the probe wire 12 which is formed with the flexible tip piece 17. The probe wire 12 is similar in construction to a metal spiral wire as commonly used for exploring the coronary vessels. The length of the flexible tip piece 17 is matched to the dimensions of the common bile duct 6 and the cystic duct 8. The length of the probe wire 12 is matched to the side-view duodenoscope. The guide catheter 10 according to FIG. 15 is similar in construction to a guide catheter as commonly used for exploring the left coronary ostium and has a length matched to the side-view duodenoscope. The guide catheter 10 is constructed similar to a usual Judkins catheter and has pre-formed bends 23, 24 which are matched to the distance between the duodenal papilla 5 and the opening of the cystic duct 8.

FIG. 16 shows a guide catheter 10 in the form of a right coronary catheter as commonly used for the exploration of the right coronary ostium, a pre-formed bend 25 being matched to the distance between the duodenal papilla 5 and the opening of the cystic duct 8, while its length is matched to the side-view duodenoscope. The irrigation catheter 13 shown in FIG. 17 carries an inflatable balloon 14 of 5–10 mm diameter and a catheter irrigation tip of 10–20 cm length with laterally arranged multiple openings 15 for irrigation and evacuation. The length of the irrigation catheter 13 is matched to that of the side-view duodenoscope 2.

We claim:

1. An apparatus for the endoscopic transpapillary exploration of a biliary tract comprising a side-view duodenoscope for insertion into the duodenum with its distal end at the duodenal papilla, a probe catheter for being slid through the side-view duodenoscope and the duodenal papilla into the common bile duct and a guide wire for arrangement in the side-view duodenoscope and the probe catheter, characterized in that the probe catheter and the guide wire are suitably constructed to be advanced as far as the cystic cut, and the apparatus includes a guide catheter to be slid over the guide wire, the guide catheter being preformed with bends corresponding to a Judkins or right coronary catheter and with a conically shaped tip for deflection into the cystic duct with the guide wire retracted, a probe wire with a flexible tip piece for being inserted through the guide catheter and through the cystic duct into the gall bladder lumen and an irrigation catheter or a small endoscope for being passed into the gall bladder lumen by means of the probe wire with the guide catheter retracted.

2. An apparatus as in claim 1, characterized in that the irrigation catheter is formed with a plurality of conduits for irrigation, evacuation and dilation.

3. An apparatus as in claim 1, characterized in that the small endoscope is provided with a guide rail or a working conduit for sliding onto the probe wire.

4. An apparatus as in claim 1, characterized in that the flexible tip piece is formed by a spiral wire and provided on its outside with a smooth plastic coating.

5. An apparatus as in claim 1, characterized in that the distal end of the probe wire is provided with a smooth round piece.

6. A method for the endoscopic transpapillary probing of a biliary tract system which comprises introducing a side-view duodenoscope into the duodenum, terminating at the duodenal papilla, advancing a probe catheter through the side-view duodenoscope and the duodenal papilla into the primary bile duct, and positioning a guide wire in the side-view duodenoscope and the probe catheter, the probe catheter and the guide wire being designed to allow insertion up to the cystic duct, advancing a guide catheter along the guide wire, the guide catheter being preformed with bends like a Judkins or right-coronary catheter and having a conically formed tip, withdrawing the guide wires so that said tip rotates in the cystic duct, inserting a probe wire with a flexible tip member through the guide catheter and the cystic duct into the gall bladder lumen, withdrawing the guide catheter and inserting a rinsing catheter or a small endoscope into the gall bladder lumen by means of a probe wire.

* * * * *